United States Patent
Baralt et al.

(10) Patent No.: US 10,961,167 B2
(45) Date of Patent: Mar. 30, 2021

(54) PROCESS FOR PREPARING HYDROCARBON MIXTURE EXHIBITING UNIQUE BRANCHING STRUCTURE

(71) Applicants: Novvi LLC, Emeryville, CA (US); Chevron U.S.A. Inc., San Ramon, CA (US)

(72) Inventors: Eduardo Baralt, Emeryville, CA (US); Cong Yan Chen, San Ramon, CA (US); Yalin Hao, San Ramon, CA (US); Liwenny Ho, Emeryville, CA (US); Willbe Ho, Emeryville, CA (US); Ajit Pradhan, San Ramon, CA (US); Jason Rosalli, Emeryville, CA (US); Benton Thomas, Emeryville, CA (US); Jason Wells, Emeryville, CA (US)

(73) Assignees: Novvi LLC, Emeryville, CA (US); Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 16/398,683

(22) Filed: Apr. 30, 2019

(65) Prior Publication Data
US 2020/0095177 A1    Mar. 26, 2020

Related U.S. Application Data

(60) Provisional application No. 62/733,698, filed on Sep. 20, 2018.

(51) Int. Cl.
*C07C 2/22* (2006.01)
*B01J 27/12* (2006.01)
(Continued)

(52) U.S. Cl.
CPC .............. *C07C 2/22* (2013.01); *B01J 21/04* (2013.01); *B01J 27/12* (2013.01); *B01J 29/7461* (2013.01);
(Continued)

(58) Field of Classification Search
CPC ........................................... C07C 2/22
See application file for complete search history.

(56) References Cited

U.S. PATENT DOCUMENTS

| | | | | |
|---|---|---|---|---|
| 5,082,986 A | * | 1/1992 | Miller | B01J 29/85 208/18 |
| 5,191,140 A | * | 3/1993 | Akatsu | B01J 27/12 585/525 |

(Continued)

FOREIGN PATENT DOCUMENTS

WO    2018089457 A2    5/2018

OTHER PUBLICATIONS

International Search Report and Written Opinion dated Jul. 11, 2019 in International Application No. PCT/US2019/029873.

*Primary Examiner* — Philip Y Louie
*Assistant Examiner* — Alyssa L Cepluch
(74) *Attorney, Agent, or Firm* — E. Joseph Gess; Melissa M. Hayworth

(57) ABSTRACT

Provided herein is a unique process that prepares a saturated hydrocarbon mixture with well-controlled structural characteristics that address the performance requirements driven by the stricter environmental and fuel economy regulations for automotive engine oils. The process allows for the branching characteristics of the hydrocarbon molecules to be controlled so as to consistently provide a composition that has a surprising CCS viscosity at −35° C. (ASTM D5329) and Noack volatility (ASTM D5800) relationship. The process comprises providing a specific olefinic feedstock, oli- (Continued)

gomerizing in the presence of a BF$_3$ catalyst, and hydroisomerizing in the presence of a noble-metal impregnated, 10-member ring zeolite catalyst.

17 Claims, 5 Drawing Sheets

(51) Int. Cl.
| | |
|---|---|
| *B01J 29/74* | (2006.01) |
| *C10M 105/04* | (2006.01) |
| *C07C 5/13* | (2006.01) |
| *B01J 21/04* | (2006.01) |
| *C07C 5/03* | (2006.01) |
| *C07C 5/25* | (2006.01) |
| *C07C 7/04* | (2006.01) |
| *C10G 67/02* | (2006.01) |
| *C10G 69/12* | (2006.01) |

(52) U.S. Cl.
CPC ............ *B01J 29/7492* (2013.01); *C07C 5/03* (2013.01); *C07C 5/13* (2013.01); *C07C 5/2556* (2013.01); *C07C 7/04* (2013.01); *C10G 67/02* (2013.01); *C10G 69/126* (2013.01); *C10M 105/04* (2013.01); *C07C 2521/02* (2013.01); *C07C 2521/12* (2013.01); *C07C 2523/38* (2013.01); *C10G 2400/22* (2013.01); *C10M 2203/024* (2013.01)

(56) References Cited

U.S. PATENT DOCUMENTS

| | | | |
|---|---|---|---|
| 6,703,356 B1 * | 3/2004 | Wu | C07C 2/12 508/591 |
| 2006/0211581 A1 * | 9/2006 | Bullock, Jr. | C10G 50/02 508/110 |
| 2007/0123659 A1 | 5/2007 | Wu et al. | |
| 2012/0115762 A1 | 5/2012 | Wang et al. | |

* cited by examiner

PROCESS FOR PREPARING HYDROCARBON MIXTURE EXHIBITING UNIQUE BRANCHING STRUCTURE

CROSS REFERENCE TO RELATED APPLICATIONS

The present application claims priority to U.S. Provisional Application No. 62/733,698 filed Sep. 20, 2018, the complete disclosure of which is incorporated herein by reference in its entirety.

FIELD OF THE INVENTION

A process has been developed for preparing high performance hydrocarbon mixtures which possess unique compositional characteristics and which demonstrate superior low temperature and volatility properties.

BACKGROUND OF THE INVENTION

Base stocks are commonly used to produce various lubricants, including lubricating oils for automobiles, industrial oils, turbine oils, greases, metal working fluids, etc. They are also used as process oils, white oils, and heat transfer fluids. Finished lubricants generally consist of two components, base oils and additives. Base oil, which could be one or a mixture of base stocks, is the major constituent in these finished lubricants and contributes significantly to their performances, such as viscosity and viscosity index, volatility, stability, and low temperature performance. In general, a few base stocks are used to manufacture a wide variety of finished lubricants by varying the mixtures of individual base stocks and individual additives.

The American Petroleum Institute (API) categorizes base stocks into five groups based on their saturated hydrocarbon content, sulfur level, and viscosity index (Table 1 below). Group I, II, and III base stocks are mostly derived from crude oil via extensive processing, such as solvent refining for Group I, and hydroprocessing for Group II and Group III. Certain Group III base stocks can also be produced from synthetic hydrocarbon liquids via a Gas-to-Liquids process (GTL), and are obtained from natural gas, coal or other fossil resources. Group IV base stocks, the polyalphaolefins (PAO), are produced by oligomerization of alpha olefins, such as 1-decene. Group V base stocks include everything that does not belong to Groups I-IV, such as naphthenic base stocks, polyalkylene glycols (PAG), and esters. Most of the feedstocks for large-scale base stock manufacturing are non-renewable.

TABLE 1

API Base Oil Classification (API 1509 Appendix E)

| API Group | Viscosity Index (ASTM D2270) | Saturates by ASTM D2007 | Sulphur, % | Description |
|---|---|---|---|---|
| I | 80-119 | <90% | >.03% | Conventional (solvent refining) |
| II | 80-119 | ≥90% | ≤.03% | Hydroprocessing |
| III | ≥120 | ≥90% | ≤.03% | Severe Hydroprocessing |
| IV | | | | PolyAlphaOlefins (PAO) |
| V | | | | All other base stocks not included above e.g. esters |

Automotive engine oils are by far the largest market for base stocks. The automotive industry has been placing more stringent performance specifications on engine oils due to requirements for lower emissions, longer drain intervals, and better fuel economy. Specifically, automotive OEMs (original equipment manufacturer) have been pushing for the adoption of lower viscosity engine oils such as 0W-20 to 0W-8, to lower friction losses and achieve fuel economy improvement. Group II's usage in 0W-xx engine oils is highly limited because formulations blended with these base stocks cannot meet the performance specifications for 0W-xx engine oils, leading to increased demands for Group III and Group IV base stocks.

Group III base stocks are mostly manufactured from vacuum gas oils (VGOs) through hydrocracking and catalytic dewaxing (e.g. hydroisomerization). Group III base stocks can also be manufactured by catalytic dewaxing of slack waxes originating from solvent refining, or by catalytic dewaxing of waxes originating from Fischer-Tropsch synthesis from natural gas or coal based raw materials also known as Gas to Liquids base oils (GTL).

Manufacturing processes of Group III base stocks from VGOs are discussed in U.S. Pat. Nos. 5,993,644 and 6,974,535. The boiling point distributions of Group III base stocks are typically higher than PAOs of the same viscosity, causing them to have higher volatility than PAOs. Additionally, Group III base stocks typically have higher cold crank viscosity (i.e., dynamic viscosity measured according to ASTM D5293, CCS) than Group IV base stocks at equivalent viscosities.

GTL base stock processing is described in U.S. Pat. Nos. 6,420,618 and 7,282,134, as well as U.S. Patent Application Publication 2008/0156697. For example, the latter publication describes a process for preparing base stocks from a Fischer-Tropsch synthesis product, the fractions of which with proper boiling ranges are subjected to hydroisomerization to produce GTL base stocks.

Structures and properties of GTL base stocks are described, for example, in U.S. Pat. Nos. 6,090,989 and 7,083,713, as well as U.S. Patent Application Publication 2005/0077208. In U.S. Patent Application Publication 2005/0077208, lubricant base stocks with optimized branching are described, which have alkyl branches concentrated toward the center of the molecules to improve the base stocks' cold flow properties. Nevertheless, pour points for GTL base stocks are typically worse than PAO or other synthetic hydrocarbon base stocks.

A further concern with GTL base stocks is the severely limited commercial supply, a result of the prohibitively large capital requirements for a new GTL manufacturing facility. Access to low cost natural gas is also required to profitably produce GTL base stocks. Additionally, as GTL base stocks are typically distilled from an isomerized oil with a wide boiling point distribution, the process results in a relatively low yield to the base stock with a desired viscosity when compared to that of a typical PAO process. Due to these monetary and yield constraints there is currently only a single manufacturing plant of group III+ GTL base stocks, exposing formulations that use GTL to supply chain and price fluctuation risks.

Polyalphaolefins (PAOs), or Group IV base oils, are produced by polymerizing alphaolefins in the presence of a Friedel Crafts catalyst such as $AlCl_3$, $BF_3$, or $BF_3$ complexes. For example, 1-octene, 1-decene, and 1-dodecene have been used to manufacture PAOs that have a wide range of viscosities, varying from low molecular weight and low viscosity of about 2 cSt at 100° C., to high molecular weight, viscous materials with viscosities exceeding 100 cSt at 100° C. The polymerization reaction is typically conducted in the absence of hydrogen; the lubricant range products are thereafter polished or hydrogenated to reduce the residual unsaturation. Processes to produce PAO based lubricants are disclosed, for example, in U.S. Pat. Nos. 3,382,291; 4,172,855; 3,742,082; 3,780,128; 3,149,178; 4,956,122; 5,082,986; 7,456,329; 7,544,850; and U.S. Patent Application Publication 2014/0323665.

To meet the increasingly stringent performance requirements of automotive engine oils and other modern lubricants, low-viscosity polyalphaolefin base stocks derived from 1-decene have been particularly favored. They are used either alone or in blends with other mineral base stocks in the lubricant formulations. However, the 1-decene based polyalphaolefins can be prohibitively expensive due to the limited supply of 1-decene. Attempts to overcome the availability constraint of 1-decene have led to the production of PAOs from C8 through C12 mixed alpha-olefin feeds, lowering the amount of 1-decene that is needed to impart the properties. However, they still do not completely remove the requirement for providing 1-decene as the predominate olefin feedstock due to performance requirements.

Alternatively, PAOs made with linear alphaolefins in the C14-C20 range have unacceptably high pour points, which are unsuitable for use in a variety of lubricants, including 0W-xx engine oils.

Therefore, there remains a need for cost-effective manufacturing processes that yield a base stock composition having superior properties for use in most-stringent automotive and other lubricant applications, with such properties including one or more of viscosity, Noack volatility, and low temperature fluidity.

In addition to the technical demands for the automotive industry, environmental awareness and regulations are driving manufacturers to use renewable feedstocks and raw materials in the production of base stocks and lubricants. Processes which can provide the desired base stocks while also exploiting the use of renewable feedstocks would be greatly welcome.

SUMMARY OF THE INVENTION

The present invention relates to a unique process that prepares a saturated hydrocarbon mixture with well-controlled structural characteristics that address the performance requirements driven by the stricter environmental and fuel economy regulations for automotive engine oils. The process allows for the branching characteristics of the hydrocarbon molecules to be controlled so as to consistently provide a composition that has a surprising CCS viscosity at −35° C. (ASTM D5329) and Noack volatility (ASTM D5800) relationship.

In one aspect, the present process comprises of providing an olefinic feedstock of C14 to C20 olefins having less than 40 wt % branched olefins and greater than 50% alpha olefins. The feedstock is oligomerized in the presence of a boron trifluoride catalyst at a reaction temperature in the range of 20-60° C. Oligomerized product is then hydroisomerized in the presence of a noble-metal impregnated, 10 member ring zeolite catalyst.

The resulting product is a saturated hydrocarbon mixture having greater than 80% of the molecules with an even carbon number according to FIMS. When the hydrocarbon mixture is analyzed by carbon NMR, it exhibits a branching characteristic of BP/BI≥−0.6037 (Internal alkyl branching per molecule)+2.0, and has on average at least 0.3 to 1.5 5+ methyl branches per molecule.

In another aspect, the process further comprises recovering a product from the oligomerization and removing unreacted monomer from the product as an olefin before the hydroisomerization. The recovered product from which the unreacted monomer has been removed is then separated into two product fractions, with one fraction comprising greater than 95 wt % dimers having a maximum carbon number of 40, and a product fraction comprising greater than 95% trimers and higher oligomerized compounds having a minimum carbon number of 42. The two fractions are hydroisomerized separately. In still another aspect, the dimer fraction separated comprising greater than 95 wt % dimers, if hydrogenated without hydroizomerization, has a branching proximity of 27 to 35.

Another aspect, provided is a process providing an olefinic feedstock comprising less than 8 wt % branched monomeric olefins and greater than 90 wt % monomeric alpha olefins, with the monomeric olefins having a carbon number in the range of from C14-C20. An oligomerization reaction is conducted with the olefinic feedstock at a temperature in the range of 20-60° C., in the presence of $BF_3$ and BuOH/BuAc co-catalyst, with a reaction residence time of from 60-180 minutes, in a semi-batch or continuous stirred tank reactor. A product is recovered from the oligomerization reaction and unreacted olefin monomer is removed by distillation. A bottom product is recovered from the distillation and the product is hydroisomerized over a noble-metal impregnated, one-dimensional zeolite with a 10-member ring at a pressure in the range of 100-800 psig; a temperature in the range of from 290-350° C.; and a hydrogen flow rate of 500-3500 scf/bbl. Following hydroisomerization the product is distilled into two fractions. One fraction comprising of approximately greater than 95 wt % dimers and a second fraction comprising of approximately greater than 95 wt % trimers and higher oligomers. In another aspect, the product recovered from the oligomerization has the unreacted monomer olefin removed by distillation, and the bottoms are hydrogenated and then hydroisomerized before the final production distillation.

DETAILED DESCRIPTION

Figure 1:
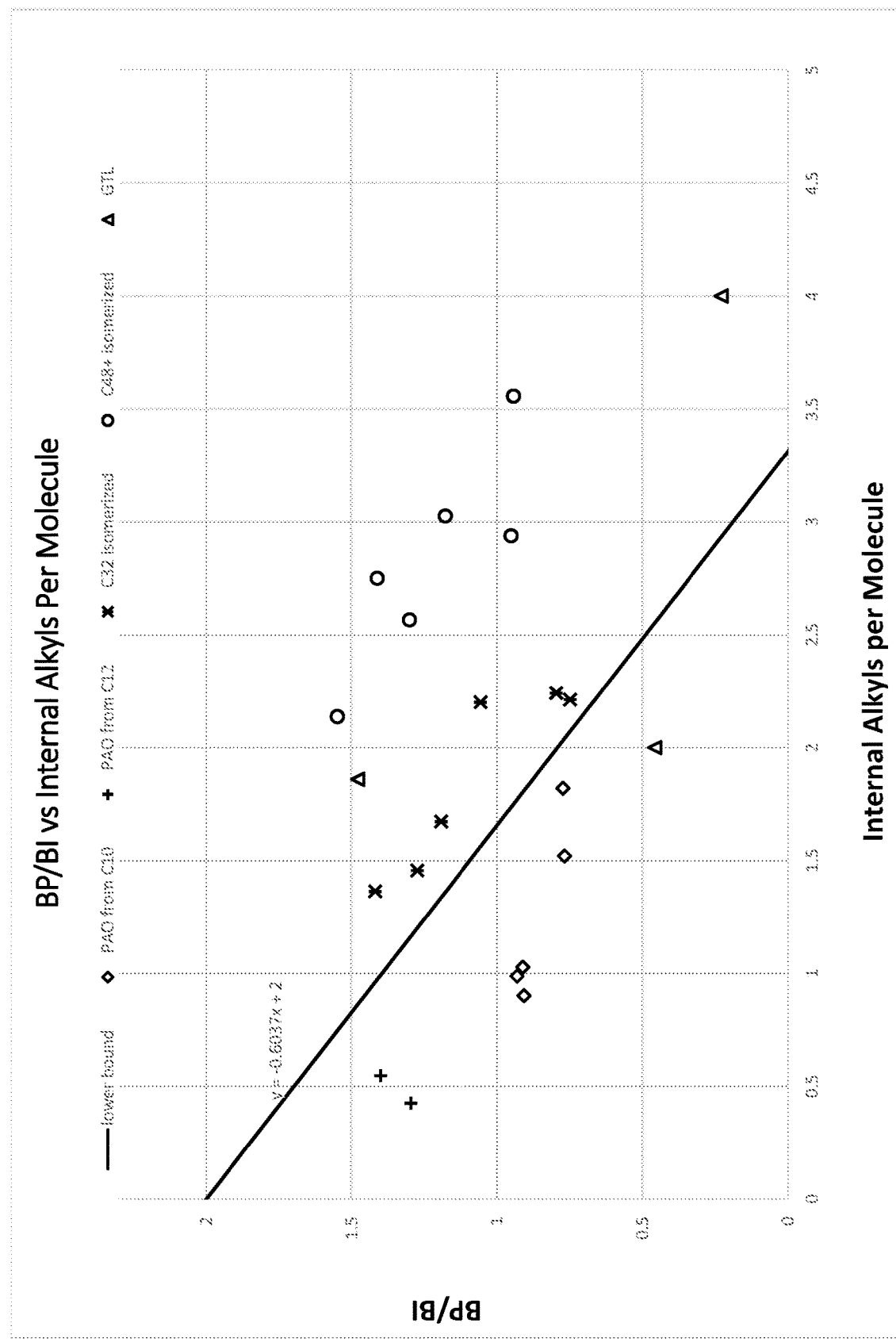
FIG. 1 illustrates the relationship between BP/BI and Internal Alkyl Branches per Molecule for various hydrocarbons, including low-viscosity PAO manufactured from 1-decene and 1-dodecene, GTL base oils, and hydroisomerized hexadecene oligomers. The straight line in the plot depicts the equation of BP/BI=−0.6037 (Internal alkyl branching per molecule)+2.0.

Disclosed herein is a process for preparing a saturated hydrocarbon mixture having a unique branching structure as characterized by NMR that makes it suitable to be used as a high-quality synthetic base stock. The process comprises oligomerizing C14 to C20 olefin to form an oligomer product consisting of unreacted monomer, dimers (C28-C40), and trimers and higher oligomers (≥C42). The unreacted monomers can be distilled off for possible re-use in a subsequent oligomerization. The remaining oligomers are then hydroisomerized to achieve the final hydrocarbon mixture having unique branching structures.

To be specific, the hydrocarbon mixture comprises greater than 80% of the molecules with an even carbon number according to FIMS. The branching characteristics of the hydrocarbon mixture by NMR indicates a BP/BI in the range ≥−0.6037 (Internal alkyl branching per molecule)+2.0. Moreover, on average, at least 0.3 to 1.5 of the internal methyl branches are located more than four carbons away from the end carbon. A saturated hydrocarbon with this unique branching structure exhibits a surprising cold crank simulated viscosity (CCS) vs. Noack volatility relationship that is beneficial for blending low-viscosity automotive engine oils.

Provided herein are processes or methods to make hydrocarbon mixtures having unique branching structures with associated beneficial properties. The hydrocarbon mixtures can be synthesized via olefin oligomerization to achieve the desired carbon chain length, followed by hydroisomerization to improve their cold-flow properties, such as pour point and CCS, etc.

In one embodiment, olefins with 14-20 carbons in length are oligomerized in the presence of a boron trifluoride acid catalyst to form an oligomer mixture. The olefins can be sourced from natural occurring molecules, such as crude oil or gas based olefins, or from ethylene polymerizations. In some variations, about 100% of the carbon atoms in the olefin feedstocks described herein may originate from renewable carbon sources. For example, an alpha-olefin monomer may be produced by oligomerization of ethylene derived from dehydration of ethanol produced from a renewable carbon source. In some variations, an alpha-olefin monomer may be produced by dehydration of a primary alcohol other than ethanol that is produced from a renewable carbon source. Said renewable alcohols can be dehydrated into olefins, using gamma alumina or sulfuric acid. In some embodiments, modified or partially hydrogenated terpene feedstocks derived from renewable resources are coupled with one or more olefins that are derived from renewable resources.

The mixture of C14-C20 olefins to create an olefinic feedstock can be selected from the group consisting of 1-tetradecene, 1-pentadecene, 1-hexadecene, 1-heptadecene, 1-octadecene, 1-eicosene (and/or optionally branched structural isomers of these olefins) and/or internal olefins derived from linear internal or branched internal pentadecenes, hexadecenes, heptadecenes, octadecenes, and eicosene. In one embodiment, the olefin monomers of the feed mixture may be selected from the group consisting of unsaturated, linear alpha-olefins, unsaturated, linear internal olefins, branched alpha olefins, branched internal olefins, and combinations thereof. In yet another embodiment, the olefin monomers of the feed mixture may comprise a mixture of linear alpha olefins and/or linear internal olefins. According to certain embodiments, the longer linear paraffin branches produced from C14-C20 olefins increases the VI and reduce the CCS of the oligomers, while the pour point of the oligomers can be reduced by the introduction of branching through isomerization of the dimer.

In one embodiment of the invention the olefinic feedstock consists of olefins from 14 to 20 carbons in length comprising of less than 40 wt % branched content. In yet another embodiment of the invention the olefinic feedstock comprises of olefins with less than 30% branched content. In yet another embodiment the olefinic feedstock comprises of olefins with less than 20% branched content. In yet another embodiment the olefinic feedstock comprises of olefins with less than 8% branched content. In a preferred embodiment the olefinic feedstock comprises of less than 3 wt % branched content. Branching in an olefin will decrease the linearity of the resulting oligomer from an oligomerization reaction. The branching imparted to the oligomer through branched olefins will decreased viscosity index without sufficiently reducing the cold flow properties such as pour point and CCS.

In one embodiment of the invention the olefinic feedstock contains at least 50% alpha olefins. In yet another embodiment the olefinic feedstock contains at least 70% alpha olefins. In yet another embodiment the olefinic feedstock contains at least 80% alpha olefins. In a preferred embodiment the olefinic feedstock contains at least 90% alpha olefins. Oligomerization of an olefinic feedstock without enough alpha olefin content will reduce the linearity of the oligomer. Depending on the double bond position on the carbon chain of the monomeric feedstock, the branching proximity of the oligomer could be reduced compared to an oligomer made from alpha olefins of an equivalent chain length. While the presence of long chain branching will reduce the pour point, it will also lead to the undesired reduction of viscosity index and increase of CCS.

In addition to the olefinic feedstock, the oligomerization conditions have strong impacts on the structure and properties of the oligomer products. In one embodiment, an olefin monomer between C14 to C20 is oligomerized in the presence of $BF_3$ and/or $BF_3$ promoted with a mixture of an alcohol and/or an ester, such as a linear alcohol and an alkyl acetate ester, in a continuously stirred tank reactor (CSTR) with an average residence time of 60 to 400 minutes. In another embodiment, the C14 to C20 olefin monomers are oligomerized in the presence of $BF_3$ and/or promoted $BF_3$ in a CSTR with an average residence time of 90 to 300 minutes. In yet another embodiment, the C14 to C20 the olefin monomers are oligomerized in the presence of $BF_3$ and/or promoted $BF_3$ in a CSTR with an average residence time of 120 to 240 minutes. The temperature of the oligomerization reaction may be in a range of from 10° C. to 90° C. However, in one preferred embodiment, the temperature is maintained in the range of from 15 to 75° C., and most preferably 20° C. to 60° C., for the duration of the reaction. It was discovered that the reaction temperature has a strong impact on the degree of isomerization taking place during the oligomerization process. Higher temperature oligomerization would increase isomerization and lead to a more branched oligomer product, which is evidenced by the reduction of the branching proximity for the saturated dimer intermediate. Where the saturated dimer intermediate is defined as oligomerization dimer, it has been isolated by distillation to <5% trimer or greater oligomers and hydrogenated without isomerization. Such branched dimers do not have the desired structure, such as 5+ methyl branching per molecule, nor do they pose the required linearity to be used as an ideal hydroisomerization feed, i.e., an oligomers created at too high of a temperature would yield undesirable physical properties such as lower viscosity index and higher Noack volatility after hydroisomerization, in comparison to those obtained from hydroisomerization of a more linear dimer fraction to the same pour point. Direct effects of oligomerization reaction temperatures are illustrated in examples 14-16.

Proper control of the oligomerization reaction temperature and residence time within a CSTR is needed to ensure the dimer portion (C28-C40) of the oligomerization product has branching proximity (BP) between 25 to 35, preferably between 27 to 35, more preferably between 27-33, and most preferably between 28-32, if the dimer portion were to be saturated to a Br index of less than 100 mg $Br_2$/100 g (ASTM D2710). A branching proximity which is too low prior to hydroisomerization will lead to isomerized hydrocarbon mixtures that fall under the solid line in FIG. 1 and will result in a less desirable higher CCS viscosity at −35° C. value for a given Noack volatility to fit within the range shown in FIG. 3. Conversely, a branching proximity which is too high will require greater isomerization to reach an acceptable pour point, which will increase the Noack volatility and the CCS at −35° C. simultaneously.

In one embodiment, the unsaturated oligomer product is distilled to remove the unreacted monomer as an olefin. For example, the unreacted monomer may be separated from the oligomer product, such as via distillation, and can be recycled back into the olefin feed stock for oligomerization thereof.

The oligomer product is then hydroisomerized to provide the additional branches required to achieve the ideal branching characteristics. In one embodiment, the whole oligomer product, including both the dimers (C28-C40) and heavier oligomers (≥C42), are hydroisomerized prior to separation by distillation. The hydroisomerized product is then separated into the final hydrocarbon products by distillation. In another embodiment, the dimers and heavier oligomers are fractionated and hydroisomerized separately.

Hydroisomerization catalysts useful in the present invention usually comprises a shape-selective molecular sieve, a metal or metal mixture that is catalytically active for hydrogenation, and a refractory oxide support. The presence of a hydrogenation component leads to improvement in product stability. Typical catalytically active hydrogenation metals include chromium, molybdenum, nickel, vanadium, cobalt, tungsten, zinc, platinum, and palladium. Platinum and palladium are especially preferred, with platinum mostly preferred. If platinum and/or palladium is used, the metal content is typically in the range of 0.1 to 5 weight percent of the total catalyst, usually from 0.1 to 2 weight percent, and not to exceed 10 weight percent. Hydroisomerization catalysts are discussed, for example, in U.S. Pat. Nos. 7,390,763 and 9,616,419, as well as U.S. Patent Application Publications 2011/0192766 and 2017/0183583.

The conditions for hydroisomerization are tailored to achieve an isomerized hydrocarbon mixture with specific branching properties, as described above, and thus will depend on the characteristics of feed used. The reaction temperature is generally between about 200° C. and 400° C., preferably between 260° C. to 370° C., most preferably between 288° C. to 345° C., at a liquid hourly space velocity (LHSV) generally between about 0.5 $hr^{-1}$ and about 5 $hr^{-1}$. The pressure is typically from about 15 psig to about 2500 psig, preferably from about 50 psig to about 2000 psig, more preferably from about 100 psig to about 1500 psig, most preferably 100 to 800 psig. Low pressure provides enhanced isomerization selectivity, which results in more isomerization and less cracking of the feed, thus leading to an increased yield of hydrocarbon mixture in the base stock boiling range.

Hydrogen is present in the reaction zone during the hydroisomerization process, typically in a hydrogen to feed ratio from about 0.1 to 10 MSCF/bbl (thousand standard cubic feet per barrel), preferably from about 0.3 to about 5 MSCF/bbl. Hydrogen may be separated from the product and recycled to the reaction zone.

In one embodiment, an additional step of hydrogenation is added before hydroisomerization to protect the downstream hydroisomerization catalyst. In another embodiment, an additional step of hydrogenation or hydrofinishing is added after the hydroisomerization to further improve the saturation and stability of the hydrocarbon mixture.

The hydroisomerized hydrocarbon mixtures are comprised of dimers having carbon numbers in the range of C28-C40, and a mixture of trimers+ having carbon numbers of C42 and greater. Each of the hydrocarbon mixtures will exhibit a BP/BI in the range of ≥−0.6037 (internal alkyl branching)±2.0 per molecule, and, on average, from 0.3 to 1.5 methyl branches on the fifth or greater position per molecule. Importantly, at least 80% of the molecules in each composition also have an even carbon number as determined by FIMS. In another embodiment, each of the hydrocarbon compositions will also exhibit a Noack and CCS at −35° C. relationship such that the Noack is between 2750 (CCS at −35° C.)$^{(-0.8)}$±2. These characteristics allow for the formulation of low-viscosity engine oils as well as many other high-performance lubricant products.

In one embodiment, C16 olefins are used as the feed for the oligomerization reaction. When using C16 olefins as the feed, the hydroisomerized dimer product generally exhibits a KV100 of 4.3 cSt with <8% Noack loss and a CCS at −35° C. of approximately 1,700 cP. The extremely low Noack volatility is due to the high initial boiling point and narrow boiling point distribution when compared other 3.9 to 4.4 cSt synthetic base stocks. This makes the dimer product ideal for use in low viscosity engine oils with strict volatility requirements. The excellent CCS and pour point characteristics are due to the branching characteristics discussed above. In one embodiment, the dimer product has a pour point of ≤−40° C. This is required to pass critical engine oil formulation requirements for 0W formulations, including Mini-Rotary Viscosity (ASTM D4684) and Scanning Brookfield Viscosity (ASTM D2983) specifications.

Different embodiments of the present process are depicted in block diagrams FIGS. 4-7.

Figure 4:
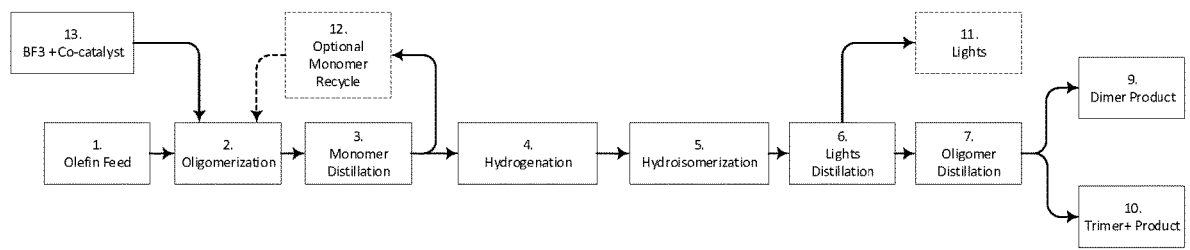
FIG. 4 depicts one embodiment of the present process where a dimer product and trimer product are separated after hydroisomerization. The oligomers are also hydrogenated prior to hydroisomerization.

FIG. 4 depicts a preferred embodiment including the selection of an olefin feed using a mixture or single olefin of 14 to 20 carbons in length (1). Oligomerizing said olefins in the presence of $BF_3$ and a promoter (13) in either semi-batch or CSTR mode (2). Subsequently, removing the unreacted monomer olefin by distillation (3). Optionally, the unreacted monomer can be recycled back into the oligomerization reactor (12). The dimer and higher oligomers are then simultaneously saturated (4) and hydroisomerized (5). Cracked light products (11) formed during hydroisomerization are removed by distillation (6). The remaining oligomers are then separated via distillation (7) into the final dimer (9) and trimer+ products (10).

Figure 5:
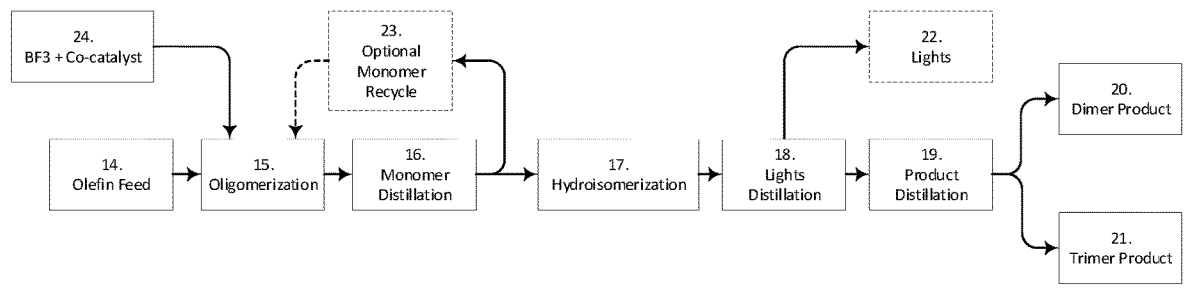
FIG. 5 depicts another embodiment of the present process where a dimer product and trimer product are separated after hydroisomerization. The oligomers are not saturated prior to the hydroisomerization step.

FIG. 5 depicts an embodiment involving the selection of an olefin feed using a mixture or single olefin of 14 to 20 carbons in length (14). Oligomerizing said olefins in the presence of $BF_3$ and a promoter (24) in either semi-batch or CSTR mode (15). Subsequently, removing the unreacted monomer by distillation (16). Optionally, the unreacted olefin monomer can be recycled back into the oligomerization reactor (23). The dimer and higher oligomers are then hydroisomerized (17). Full saturation of the isomerized oligomers is achieved during the hydroisomerization process (17). Cracked light products (22) formed during hydroisomerization are removed (18). The remaining oligomers are then separated via distillation (19) into the final dimer (20) and trimer+ products (21).

Figure 6:
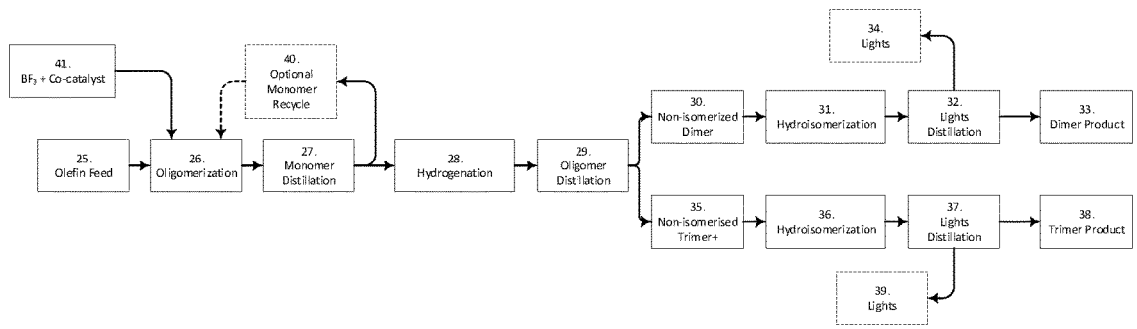
FIG. 6 depicts an embodiment of the present process where a dimer product and a timer+ product are saturated and separated prior to hydroisomerization. Each product is then hydroisomerized separately.

FIG. 6 depicts a variation on the process where the oligomerization product is saturated (28) and distilled (29) prior to the hydroisomerization. The non-isomerized hydrogenated dimers (30) have a branching proximity between 27-35. The non-isomerized dimer (30) and trimer+(35) products are then hydroisomerized (31, 36) separately and the resulting cracked light streams (34, 39) are removed via distillation (32, 37) to yield the final dimer (33) and trimer+ (38) products.

Figure 7:
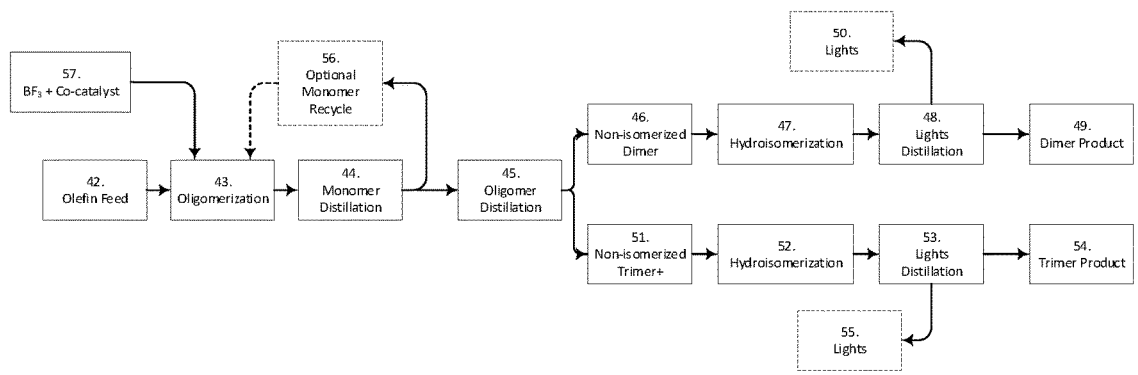
FIG. 7 depicts a variation of the process in FIG. 6, where the oligomers are not hydrogenated prior to separation and hydroisomerization.

FIG. 7 depicts a variation on the process where the oligomer distillation (45) to separate the non-isomerized dimers from the trimer+ oligomers (46, 51), is done prior to hydroisomerization. Full saturation of both the dimer and trimer+ fraction is achieved during the hydroisomerization process (47, 52). The cracked lights (50, 55) are then removed from the hydroisomerized dimers and trimers by distillation (48, 53) to yield the final dimer (49) and trimer+ (54) products.

Figure 2:
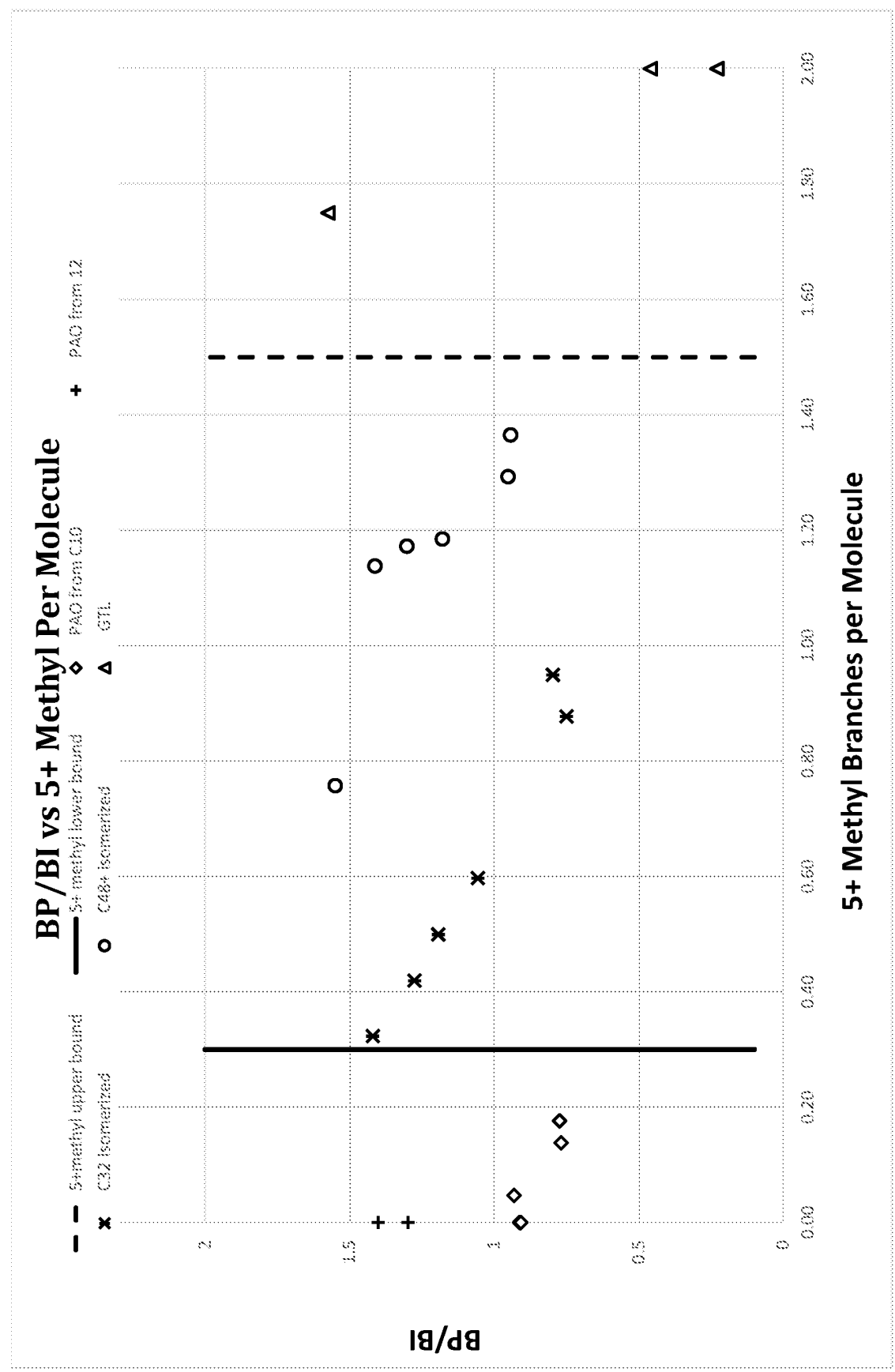
FIG. 2 illustrates the relationship between BP/BI and 5+ Methyl Branches per Molecule for various hydrocarbons, including low-viscosity PAO manufactured from 1-decene and 1-dodecene, GTL base oils, and hydroisomerized hexadecene oligomers. It demonstrates that the 5+ Methyl Branches per Molecules for the hydrocarbon mixtures disclosed in this patent fall in a unique range of 0.3-1.5.
Figure 3:
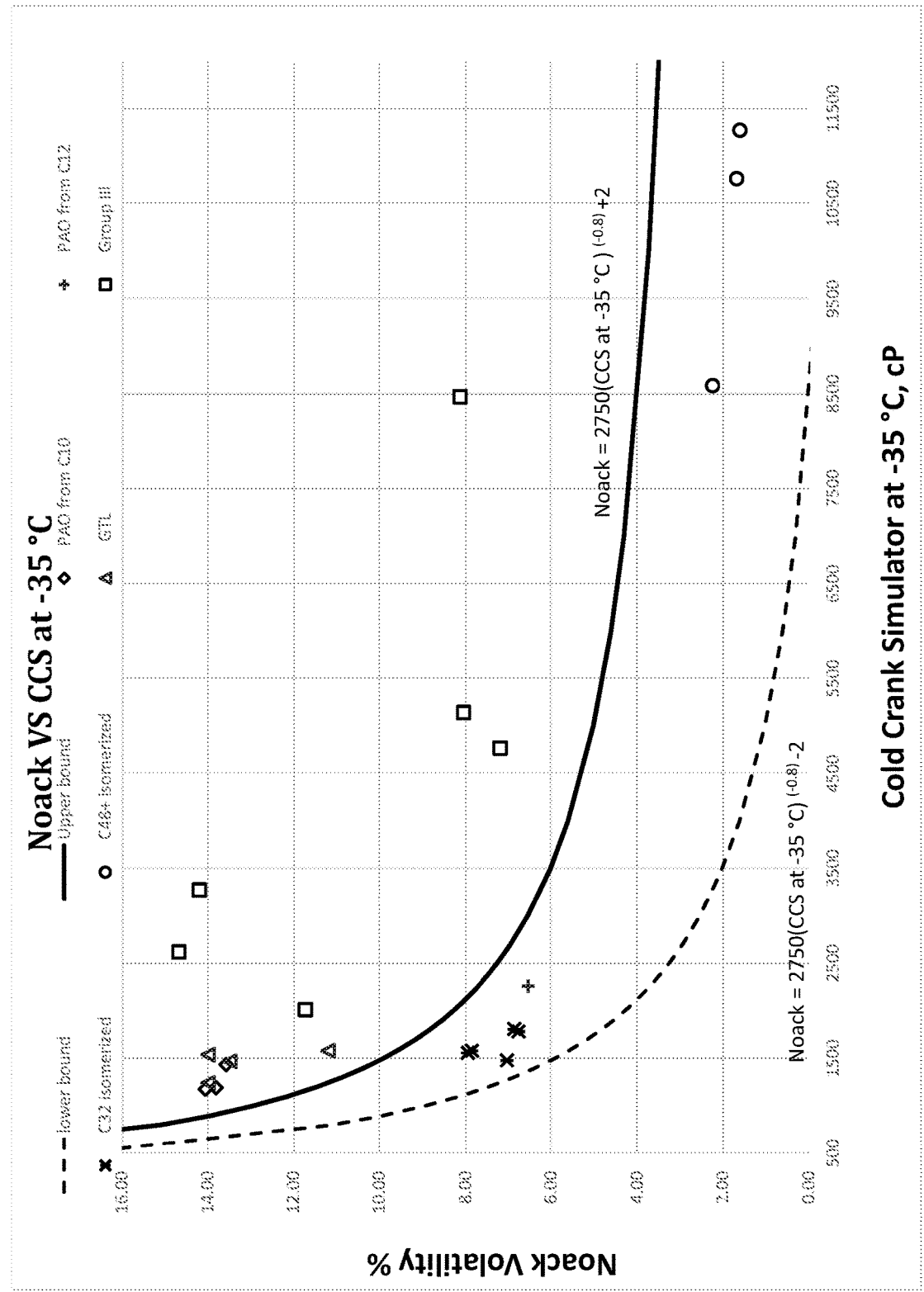
FIG. 3 illustrates the relationship between NOACK volatility and CCS at −35° C. for various hydrocarbons, including low-viscosity PAO manufactured from 1-decene and 1-dodecene, GTL base oils, Group III base oils, and hydroisomerized hexadecene oligomers. The solid line and dotted line depicts the upper limit and lower limit of the Noack vs. CCS at −35° C. exhibited by the present unique hydrocarbon mixture, which are NOACK=2,750 (CCS at −35° C.)$^{(-0.8)}$+2 and NOACK=2,750 (CCS at −35° C.)$^{(-0.8)}$−2, respectively.

As noted, the resulting hydrocarbon mixture obtained from the present process has outstanding properties including extremely low volatility, good low-temperature properties, etc., which are important performance attributes of high-quality base stocks. To be specific, the mixture comprises greater than 80% of the molecules with an even carbon number according to FIMS. The branching characteristics of the hydrocarbon mixture by NMR indicates a BP/BI in the range $\geq -0.6037$ (Internal alkyl branching per molecule)+2.0. Moreover, on average, at least 0.3 to 1.5 of the internal methyl branches are located more than four carbons away from the end carbon. These characteristics are illustrated in FIGS. 1-3 of the drawings. A saturated hydrocarbon with this unique branching structure exhibits a surprising cold crank simulated viscosity (CCS) vs. Noack volatility relationship (FIG. 3) that is beneficial for blending low-viscosity automotive engine oils. The following definitions are offered to better understand the uniqueness of the hydrocarbon mixture product achieved by the present process.

Definitions of Hydrocarbon Properties

The following properties are used in describing the novel saturated hydrocarbon mixtures:

Viscosity is the physical property that measures the fluidity of the base stock. Viscosity is a strong function of temperature. Two commonly used viscosity measurements are dynamic viscosity and kinematic viscosity. Dynamic viscosity measures the fluid's internal resistance to flow. Cold cranking simulator (CCS) viscosity at −35° C. for engine oil is an example of dynamic viscosity measurements. The SI unit of dynamic viscosity is Pa·s. The traditional unit used is centipoise (cP), which is equal to 0.001 Pa·s (or 1 m Pa·s). The industry is slowly moving to SI units. Kinematic viscosity is the ratio of dynamic viscosity to density. The SI unit of kinematic viscosity is $mm^2/s$. The other commonly used units in industry are centistokes (cSt) at 40° C. (KV40) and 100° C. (KV100) and Saybolt Universal Second (SUS) at 100° F. and 210° F. Conveniently, 1 $mm^2/s$ equals 1 cSt. ASTM D5293 and D445 are the respective methods for CCS and kinematic viscosity measurements.

Viscosity Index (VI) is an empirical number used to measure the change in the base stock's kinematic viscosity as a function of temperature. The higher the VI, the less relative change is in viscosity with temperature. High VI base stocks are desired for most of the lubricant applications, especially in multigrade automotive engine oils and other automotive lubricants subject to large operating temperature variations. ASTM D2270 is a commonly accepted method to determine VI.

Pour Point is the lowest temperature at which movement of the test specimen is observed. It is one of the most important properties for base stocks as most lubricants are designed to operate in the liquid phase. Low pour point is usually desirable, especially in cold weather lubrication. ASTM D97 is the standard manual method to measure pour point. It is being gradually replaced by automatic methods, such as ASTM D5950 and ASTM D6749. ASTM D5950 with 1° C. testing interval is used for pour point measurement for the examples in this patent.

Volatility is a measurement of oil loss from evaporation at an elevated temperature. It has become a very important specification due to emission and operating life concerns, especially for lighter grade base stocks. Volatility is dependent on the oil's molecular composition, especially at the front end of the boiling point curve. Noack (ASTM D5800) is a commonly accepted method to measure volatility for automotive lubricants. The Noack test method itself simulates evaporative loss in high temperature service, such as an operating internal combustion engine.

Boiling point distribution is the boiling point range that is defined by the True Boiling Points (TBP) at which 5% and 95% materials evaporates. It is measured by ASTM D2887 herein.

NMR Branching Analysis:

All branching parameters are to be measured on hydrocarbons with <1000 Br index mg Br/100 g. Branching parameters measured by NMR spectroscopy for the hydrocarbon characterization include:

Branching Index (BI): the percentage of methyl hydrogens appearing in the chemical shift range of 0.5 to 1.05 ppm among all hydrogens appearing in the 1H NMR chemical range 0.5 to 2.1 ppm in an isoparaffinic hydrocarbon.

Branching Proximity (BP): the percentage of recurring methylene carbons which are four or more number of carbon atoms removed from an end group or branch appearing at $^{13}C$ NMR chemical shift 29.8 ppm.

Internal Alkyl Carbons: is the number of methyl, ethyl, or propyl carbons which are three or more carbons removed from end methyl carbons, that includes 3-methyl, 4-methyl, 5+ methyl, adjacent methyl, internal ethyl, n-propyl and unknown methyl appearing between $^{13}$C NMR chemical shift 0.5 ppm and 22.0 ppm, except end methyl carbons appearing at 13.8 ppm.

5+ Methyl Carbons: is the number of methyl carbons attached to a methine carbon which is more than four carbons away from an end carbon appearing at 13C NMR chemical shift 19.6 ppm in an average isoparaffinic molecule.

The feedstock can be defined in terms of alpha, branched and internal olefins.

Catalyst definition: Butanol and Butyl Acetate are to be described as n-Butanol and Butyl Acetate as n-Butyl-Acetate.

Alpha-olefin: unsaturated hydrocarbon with a chemical formula $C_xH_{2x}$, distinguished by having a double bond at the primary or alpha position and having a linear hydrocarbon chain.

Branched olefin: an olefin in which the carbon structure has one or more tertiary carbons.

Internal olefin: an olefin in which the unsaturation is not in a terminal position.

The NMR spectra were acquired using Bruker AVANCE 500 spectrometer using a 5 mm BBI probe. Each sample was mixed 1:1 (wt:wt) with $CDCl_3$. The $^1$H NMR was recorded at 500.11 MHz and using a 9.0 μs (30°) pulse applied at 4 s intervals with 64 scans co-added for each spectrum. The $^{13}$C NMR was recorded at 125.75 MHz using a 7.0 μs pulse and with inverse gated decoupling, applied at 6 sec intervals with 4096 scans co-added for each spectrum. A small amount of 0.1 M $Cr(acac)_3$ was added as a relaxation agent and TMS was used as an internal standard.

The branching properties of the lubricant base stock samples of the present invention are determined according to the following six-step process. Procedure is provided in detail in US 20050077208 A1, which is incorporated herein in its entirety. The following procedure is slightly modified to characterize the current set of samples:

1) Identify the CH branch centers and the $CH_3$ branch termination points using the DEPT Pulse sequence (Doddrell, D. T.; D. T. Pegg; M. R. Bendall, Journal of Magnetic Resonance 1982, 48, 323ff.).
2) Verify the absence of carbons initiating multiple branches (quaternary carbons) using the APT pulse sequence (Patt, S. L.; J. N. Shoolery, Journal of Magnetic Resonance 1982, 46, 535ff.).
3) Assign the various branch carbon resonances to specific branch positions and lengths using tabulated and calculated values (Lindeman, L. P., Journal of Qualitative Analytical Chemistry 43, 1971 1245ff; Netzel, D. A., et. al., Fuel, 60, 1981, 307ff.).

Branch NMR Chemical Shift (ppm)

TABLE 2

Describes ppm shift of alkyl branching by Carbon NMR

| Branch | NMR Chemical Shift (ppm) |
|---|---|
| 2-methyl | 22.5 |
| 3-methyl | 19.1 or 11.4 |
| 4-methyl | 14.0 |
| 5+ methyl | 19.6 |
| Internal ethyl | 10.8 |
| n-propyl | 14.4 |
| Adjacent methyl | 16.7 |

4) Quantify the relative frequency of branch occurrence at different carbon positions by comparing the integrated intensity of its terminal methyl carbon to the intensity of a single carbon (total integral/number of carbons per molecule in the mixture). For example, number of 5+ methyl branches per molecule is calculated from the signal intensity at a chemical shift of 19.6 ppm relative to intensity of a single carbon.

For the unique case of the 2-methyl branch, where both the terminal and the branch methyl occur at the same resonance position, the intensity was divided by two before doing the frequency of branch occurrence calculation.

If the 4-methyl branch fraction is calculated and tabulated, its contribution to the 5+ methyls must be subtracted to avoid double counting.

Unknown methyl branches are calculated from contribution of signals that appear between 5.0 ppm and 22.5 ppm, however not including any branches reported in Table 2.

5) Calculate the Branching Index (BI) and Branching Proximity (BP) using the calculations described in U.S. Pat. No. 6,090,989, which is incorporated by reference herein in its entirety.
6) Calculate the total internal alkyl branches per molecule by adding up the branches found in steps 3 and 4, except the 2-methyl branches. These branches would include 3-methyl, 4-methyl, 5+ methyl, internal ethyl, n-propyl, adjacent methyl and unknown methyl.

FIMS Analysis: The hydrocarbon distribution of the current invention is determined by FIMS (field ionization mass spectroscopy). FIMS spectra were obtained on a Waters GCT-TOF mass spectrometer. The samples were introduced via a solid probe, which was heated from about 40° C. to 500° C. at a rate of 50° C. per minute. The mass spectrometer was scanned from m/z 40 to m/z 1000 at a rate of 5 seconds per decade. The acquired mass spectra were summed to generate one averaged spectrum which provides carbon number distribution of paraffins and cycloparaffins containing up to six rings.

Hydrocarbon Structure and Properties

The structure of the hydrocarbon mixtures disclosed herein are characterized by FIMS and NMR. FIMS analysis demonstrate that more than 80% of the molecules in the hydrocarbon mixtures have an even carbon number.

The unique branching structure of the hydrocarbon mixtures disclosed herein are characterized by NMR parameters, such as BP, BI, internal alkyl branching, and 5+ methyls. BP/BI of the hydrocarbon mixtures are in the range of ≥−0.6037 (Internal alkyl branching per molecule)+2.0. The 5+ methyls of the hydrocarbon mixtures average from 0.3 to 1.5 per molecule.

The hydrocarbon mixture can be classified into two carbon ranges based on the carbon number distribution, C28 to C40 carbons, and greater than or equal to C42. Generally, about or greater than 95% of the molecules present in each hydrocarbon mixture have carbon numbers within the specified range. Representative molecular structures for the C28 to C40 range can be proposed based on the NMR and FIMS analysis. Without wishing to be bound to any one particular theory, it is believed that the structures made by oligomerization and hydroisomerization of olefins has methyl, ethyl, butyl branches distributed throughout the structure and the branch index and branch proximity contribute to the surprisingly good low temperature properties of the product. Exemplary structures in the present hydrocarbon mixture are as follows:

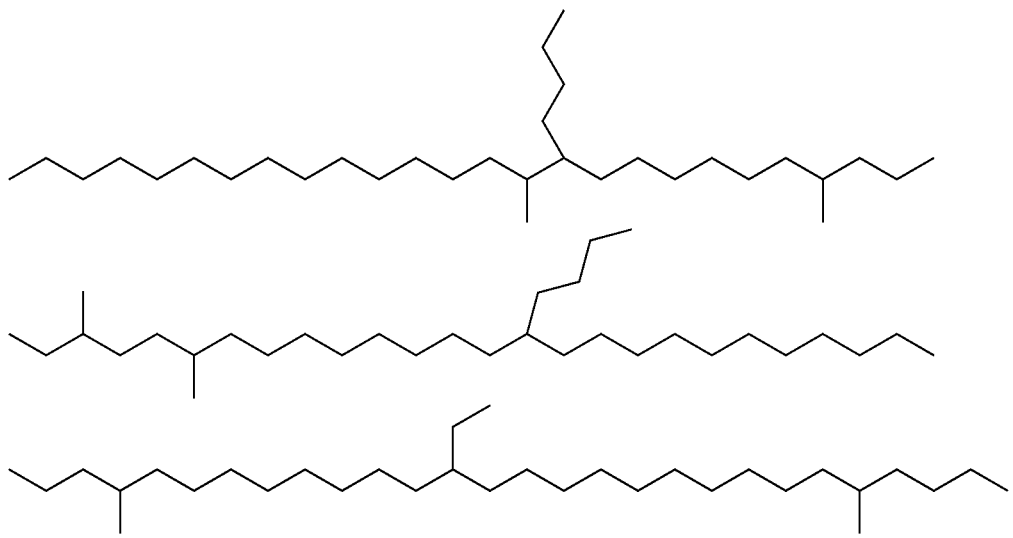

The unique branching structure and narrow carbon distribution of the hydrocarbon mixtures makes them suitable to be used as high-quality synthetic base oils, especially for low-viscosity engine oil applications. The hydrocarbon mixtures exhibit:

a KV100 in the range of 3.0-10.0 cSt;
a pour point in the range of −20 to −55° C.; and
a Noack and CCS at −35° C. relationship such that Noack is between 2750 (CCS at −35° C.)$^{(-0.8)}$±2.

The Noack and CCS relationship for the hydrocarbon mixtures are shown in FIGS. 3 and 4. In each figure, the top line represents Noack=2750 (CCS at −35° C.)$^{(-0.8)}$+2 and the bottom graph line represents Noack=2750 (CCS at −35° C.)$^{(-0.8)}$−2. More preferably the hydrocarbon mixtures have a Noack and CCS at −35 C relationship such that the Noack is between Noack=2750 (CCS at −35° C.)$^{(-0.8)}$+0.5 and Noack=2750 (CCS at −35° C.)$^{(-0.8)}$−2. Hydrocarbon mixtures that are closer to the origin in FIGS. 3 and 4 have been found more advantageous for low viscosity engine oils due to the low volatility and decreased viscosity at −35° C.

A hydrocarbon mixture in accordance with the present invention with carbon numbers in the range of C28 to C40, and in another embodiment carbon numbers in the range of from C28 to C36, or in another embodiment molecules with a carbon number of C32, will generally exhibit the following characteristics in addition to the characteristics of BP/BI, Internal alkyl branches per molecule, 5+ methyl branches per molecule, and Noack/CCS relationship described above:

a KV100 in the range of 3.0-6.0 cSt;
a VI in the range of 11 ln(BP/BI)+135 to 11 ln(BP/BI)+145; and
a pour point in the range of 33 ln(BP/BI)−45 to 33 ln(BP/BI)−35.

In one embodiment, the KV100 for the C28-C40 hydrocarbon mixture ranges from 3.2 to 5.5 cSt; in another embodiment the KV100 ranges from 4.0 to 5.2 cSt; and from 4.1 to 4.5 cSt in another embodiment.

The VI for the C28-C40 hydrocarbon mixture ranges from 125 to 155 in one embodiment and from 135 to 145 in another embodiment.

The Pour Point of the hydrocarbon mixture, in one embodiment ranges from 25 to −55° C. and from 35 to −45° C. in another embodiment.

The boiling point range of the C28-C40 hydrocarbon mixture in one embodiment is no greater than 125° C. (TBP at 95%−TBP at 5%) as measured by ASTM D2887; no greater than 100° C. in another embodiment; no greater than 75° C. in one embodiment; no greater than 50° C. in another embodiment; and no greater than 30° C. in one embodiment. In the preferred embodiments, those with a boiling point range no greater than 50° C., and even more preferably no greater than 30° C., give a surprisingly low Noack Volatility (ASTM D5800) for a given KV100.

The C28-C40 hydrocarbon mixture in one embodiment has a Branching Proximity (BP) in the range of 14-30 with a Branching Index (BI) in the range of 15-25; and in another embodiment a BP in the range of 15-28 and a BI in the range of 16-24.

The Noack volatility (ASTM D5800) of the C28-C40 hydrocarbon mixture is less than 16 wt % in one embodiment; less than 12 wt % in one embodiment; less than 10 wt % in one embodiment; less than 8 wt % in one embodiment and less than 7 wt % in one embodiment. The C28-C40 hydrocarbon mixture in one embodiment also has a CCS viscosity at −35° C. of less than 2700 cP; of less than 2000 cP in another embodiment; of less than 1700 cP in one embodiment; and less than 1500 cP in one embodiment.

The hydrocarbon mixture with the carbon number range of C42 and greater will generally exhibit the following characteristics, in addition to the characteristics of BP/BI, internal alkyl branches per molecule, 5+ methyl branches per molecule, and Noack and CCS at −35° C. relationship described above:

a KV100 in the range of 6.0-10.0 cSt;
a VI in the range of 11 ln(BP/BI)+145 to 11 ln(BP/BI)+160; and
a Pour Point in the range of 33 ln(BP/BI)−40 to 33 ln(BP/BI)−25.

The hydrocarbon mixture comprising C42 carbons or greater, in one embodiment has a KV100 in the range of 8.0 to 10.0 cSt, and in another embodiment from 8.5 to 9.5 cSt.

The VI of the hydrocarbon mixture having ≥42 carbons is 140-170 in one embodiment; and, from 150-160 in another embodiment.

The pour point in one embodiment ranges from −15 to −50° C.; and, from −20 to −40° C. in another embodiment.

In one embodiment, the hydrocarbon mixture comprising ≥42 carbons has a BP in the range of 16-30 with a BI in the range of 15-25. In another embodiment, the hydrocarbon mixture has a BP in the range of 18-28 and a BI in the range of 17-23.

In general, both hydrocarbon mixtures disclosed above exhibit the following characteristics:
- at least 80% of the molecules have an even carbon number according to FIMS;
- a KV100 in the range of 3.0-10.0 cSt;
- a pour point in the range of −20 to −55° C.;
- a Noack and CCS @ −35° C. relationship such that Noack is between 2750 (CCS@−35° C.)$^{(-0.8)}$±2;
- a BP/BI in the range of ≥−0.6037 (Internal alkyl branching)+2.0 per molecule; and
- on average from 0.3 to 1.5 5+ methyl branches per molecule.

Lubricant Formulations

The hydrocarbon mixtures prepared by the present process can be used as lubricant base stocks to formulate final lubricant products comprising additives. In certain variations, a base stock prepared according to the methods described herein is blended with one or more additional base stocks, e.g., one or more commercially available PAOs, one or more Gas to Liquid (GTL) base stocks, one or more mineral base stocks, a vegetable oil base stock, an algae-derived base stock, a second base stock as described herein, or any other type of renewable base stocks. Any effective amount of additional base stock may be added to reach a blended base oil having desired properties.

The present invention will be further illustrated by the following examples, which are not intended to be limiting.

EXAMPLES

Examples 1-6 (C28-C40 Hydrocarbon Mixtures)

Example 1

1-Hexadecene with less than 8% branched and internal olefins was oligomerized under $BF_3$ with a co-catalyst composition of Butanol and Butyl Acetate. The reaction was held at 20° C. during semi-continuous addition of olefins and co-catalyst. The residence time was 90 minutes. The unreacted monomer was then distilled off, leaving behind less than 0.1% monomer in the distillation bottoms. The dimer was then separated from the trimer+ by distillation with less than 5% trimer remained in the dimer cut.

The dimers were then hydroisomerized with a noble-metal impregnated aluminosilicate of MRE structure type catalyst bound with alumina. The reaction was carried out in a fixed bed reactor at 500 psig and 307° C. Cracked molecules were separated from the hydroisomerized C16 dimer using an online stripper.

Example 2

The oligomerization and oligomer distillation were performed identically to Example 1. The dimers were then hydroisomerized with a noble-metal impregnated aluminosilicate of MRE structure type catalyst bound with alumina. The reaction was carried out in a fix bed reactor at 500 psig and 313° C. Cracked molecules were separated from the hydroisomerized C16 dimers using an online stripper.

Example 3

The oligomerization and oligomer distillation were performed identically to Example 1. The dimers were then hydroisomerized with a noble-metal impregnated aluminosilicate of MRE structure type catalyst bound with alumina. The reaction was carried out in a fix bed reactor at 500 psig and 324° C. Cracked molecules were separated from the hydroisomerized C16 dimers using an online stripper.

Example 4

The oligomerization and oligomer distillation were performed identically to Example 1. The dimers were then hydroisomerized with a noble-metal impregnated aluminosilicate of MTT structure type catalyst bound with alumina. The reaction was carried out in a fix bed reactor at 500 psig and 316° C. Cracked molecules were separated from the hydroisomerized C16 dimers using an online stripper.

Example 5

The oligomerization and oligomer distillation were performed identically to Example 1. The dimers were then hydroisomerized with a noble-metal impregnated aluminosilicate of MTT structure type catalyst bound with alumina. The reaction was carried out in a fix bed reactor at 500 psig and 321° C. Cracked molecules were separated from the hydroisomerized C16 dimers using an online stripper.

Example 6

The oligomerization and oligomer distillation were performed identically to Example 1. The dimers were then hydroisomerized with a noble-metal impregnated aluminosilicate of MTT structure type catalyst bound with alumina. The reaction was carried out in a fix bed reactor at 500 psig and 332° C. Cracked molecules were separated from the hydroisomerized C16 dimers using an online stripper.

Examples 7-12 (C≥42 Hydrocarbon Mixtures)

Example 7

1-Hexadecene with less than 8% branched and internal olefins was oligomerized under $BF_3$ with a co-catalyst composition of Butanol and Butyl Acetate. The reaction was held at 20° C. during semi-continuous addition of olefins and co-catalyst. The residence time was 90 minutes. The unreacted monomer was then distilled off, leaving behind less than 0.1% monomer in the distillation bottoms. A subsequent distillation was performed to separate the dimer from the trimer and higher oligomers, the resulting dimer has less than 5% trimer.

The trimer and higher oligomers (trimer+) cut was then hydroisomerized with a noble-metal impregnated aluminosilicate of MRE structure type catalyst bound with alumina. The reaction was carried out in a fixed bed reactor at 500 psig and 313° C. Cracked molecules were separated from the hydroisomerized C16 trimer+ using an online stripper.

Example 8

The oligomerization and subsequent distillations were performed identically to Example 7. The trimer+ cut was then hydroisomerized with a noble-metal impregnated aluminosilicate of MRE structure type catalyst bound with alumina. The reaction was carried out in a fix bed reactor at 500 psig and 318° C. Cracked molecules were separated from the hydroisomerized C16 trimer+ using an online stripper.

Example 9

The oligomerization and subsequent distillations were performed identically to Example 7. The trimer+ cut was then hydroisomerized with a noble-metal impregnated aluminosilicate of MRE structure type catalyst bound with alumina. The reaction was carried out in a fix bed reactor at 500 psig and 324° C. Cracked molecules were separated from the hydroisomerized C16 trimer+ using an online stripper.

Example 10

The oligomerization and subsequent distillations were performed identically to Example 7. The trimer+ cut was then hydroisomerized with a noble-metal impregnated aluminosilicate of MTT structure type catalyst bound with alumina. The reaction was carried out in a fix bed reactor at 500 psig and 321° C. Cracked molecules were separated from the hydroisomerized C16 trimer+ using an online stripper.

Example 11

The oligomerization and subsequent distillations were performed identically to Example 7. The trimer+ cut was then hydroisomerized with a noble-metal impregnated aluminosilicate of MTT structure type catalyst bound with alumina. The reaction was carried out in a fix bed reactor at 500 psig and 327° C. Cracked molecules were separated from the hydroisomerized C16 trimer+ using an online stripper.

Example 12

The oligomerization and subsequent distillations were performed identically to Example 7. The trimer+ cut was then hydroisomerized with a noble-metal impregnated aluminosilicate of MTT structure type catalyst bound with alumina. The reaction was carried out in a fix bed reactor at 500 psig and 332° C. Cracked molecules were separated from the hydroisomerized C16 trimer+ using an online stripper.

Examples 13 and 14

Hexadecene with 75% alpha olefin and less than 8% branched and internal olefins was oligomerized under $BF_3$ with a co-catalyst composition of Butanol and Butyl Acetate. The reaction was held at 50° C. during semi-continuous addition of olefins and co-catalyst. The residence time was 90 minutes. The unreacted monomer was then distilled off, leaving behind less than 0.1% monomer distillation bottoms.

The dimer and higher oligomers were then hydroisomerized with a noble-metal impregnated aluminosilicate of MRE structure type catalyst bound with alumina. The reaction was carried out in a fixed bed reactor at 350 psig and 300° C. Cracked molecules were separated from the hydroisomerized C16 dimer using an online stripper. A subsequent distillation was performed to separate the dimer from the trimer+ with less than 5% trimer remained in the dimer cut. The distillation fraction containing the trimer+ was inspected and is reflected as Example 14.

Inspection results for the hydrocarbon mixtures obtained in examples 1-14 are summarized in Table 3 below.

TABLE 3

| Example | BP/BI | Internal Alkyl | 5+ Methyl | KV40, cSt | KV100, cSt | VI | Noack, wt % | Pour Point (° C.) | CCS at −35° C., cP |
|---|---|---|---|---|---|---|---|---|---|
| No. 1 | 1.42 | 1.36 | 0.32 | 18.57 | 4.306 | 144 | 6.9 | −27 | 1809 |
| No. 2 | 1.19 | 1.67 | 0.50 | 18.67 | 4.297 | 142 | NM* | −36 | 1384 |
| No. 3 | 0.80 | 2.24 | 0.95 | 19.01 | 4.290 | 136 | 7.9 | −51 | 1581 |
| No. 4 | 1.28 | 1.46 | 0.42 | 18.76 | 4.324 | 143 | 7.0 | −29 | 1480 |
| No. 5 | 1.06 | 2.20 | 0.60 | 18.85 | 4.313 | 141 | NM* | −38 | 1430 |
| No. 6 | 0.75 | 2.21 | 0.88 | 18.99 | 4.303 | 138 | 8.0 | −48 | 1558 |
| No. 7 | 1.55 | 2.14 | 0.76 | 49.66 | 8.764 | 156 | 1.6 | −19 | 26272 |
| No. 8 | 1.30 | 2.57 | 1.17 | 49.99 | 8.744 | 154 | 1.6 | −24 | 11278 |
| No. 9 | 0.94 | 3.56 | 1.37 | 50.76 | 8.730 | 151 | 1.7 | −34 | 10769 |
| No. 10 | 1.41 | 2.75 | 1.14 | 48.93 | 8.642 | 156 | 1.9 | −22 | 124967 |
| No. 11 | 1.18 | 3.03 | 1.18 | 49.09 | 8.597 | 154 | 2.3 | −28 | 18252 |
| No. 12 | 0.95 | 2.94 | 1.29 | 49.44 | 8.533 | 150 | 2.2 | −35 | 8589 |
| No. 13 | 0.77 | 2.46 | 0.92 | 19.71 | 4.386 | 135 | 7.22 | −46 | 1737 |
| No. 14 | 1.14 | 3.15 | 1.14 | 27.45 | 5.567 | 146 | 2.0 | −30 | 11105 |

*NM: not measured

In FIGS. 1 and 2, the relationship between BP/BI and internal alkyl branches per molecule, and 5+ methyl branches per molecule, respectively, is demonstrated for the hydrocarbon mixtures achieved by the present process. FIG. 3 graphically depicts the relationship between NOACK volatility and CCS at −35° C. for the hydrocarbon products obtained. The data in Table 3 confirms these unique relationships and characteristics.

Examples 15-21

Impact of boron triflouride oligomerization reaction temperatures on the oligomer structure and properties was studied. Higher reaction temperature was found to increase the isomerization taking place during the oligomerization. To directly observe this effect by NMR, oligomer products were saturated and distilled into dimer and trimer+ fractions.

The branching proximity for each dimer fraction example was measured. The results are shown below in Table 4 for samples 15 through 21.

TABLE 4

| Example# | reaction temperature (° C.) | % alpha Olefin | Branching Proximity | Branching Index | 5+ Methyl | KV100 | VI | PP (° C.) |
|---|---|---|---|---|---|---|---|---|
| Example #15 | 30 | 93 | 30.6 | 17.4 | 0.06 | 4.29 | 151 | −15 |
| Example #16 | 50 | 93 | 28.7 | 19.5 | 0.08 | 4.33 | 148 | −18 |
| Example #17 | 80 | 93 | 26.5 | 20.5 | 0.27 | 4.35 | 143 | −18 |
| Example #18 | 50 | 75 | 29.3 | 19.2 | 0.23 | 4.28 | 145 | −18 |
| Example #19 | 50 | 60 | 31.6 | 18.69 | 0.1 | 4.33 | 144 | −18 |
| Example #20 | 30 | 60 | 30.5 | 19.1 | 0.12 | 4.31 | 147 | −18 |
| Example #21 | 50 | 45 | 29.9 | 19.5 | 0.18 | 4.33 | 144 | −21 |

From the data it can be seen that as reaction temperature increases the linearity of the fraction, as measured by Branching Proximity, is decreased. This indicates an increase in the number of branches along the carbon backbone. The increased branching that results during high temperature oligomerization does not provide the dimer fraction with the required number of 5+ methyl branching per molecule needed to obtain a desirable pour point. The desired 5+ methyl branching is achieved through hydroisomerization of the oligomer product.

Increases in the methyl branching during oligomerization will result in hydroisomerized product with incorrect branching and non-ideal physical properties. A branching proximity of between 27-35 is required of the hydrogenated dimer prior to hydroisomerization.

Example 15

Hexadecene with 93% alpha olefin and less than 8% branched and internal olefins was oligomerized under $BF_3$ with a co-catalyst composition of Butanol and Butyl Acetate. The reaction was held at 30° C. during semi-continuous addition of olefins and co-catalyst. The residence time was 90 minutes. The unreacted monomer was then distilled off, leaving behind less than 0.1% monomer distillation bottoms. A subsequent distillation was performed to separate the dimer from the trimer+ with less than 5% trimer remained in the dimer cut. The dimer cut was subsequently hydrogenated without isomerization.

Example 16

Hexadecene with 93% alpha olefin and less than 8% branched and internal olefins was oligomerized under $BF_3$ with a co-catalyst composition of Butanol and Butyl Acetate. The reaction was held at 50° C. during semi-continuous addition of olefins and co-catalyst. The residence time was 90 minutes. The unreacted monomer was then distilled off, leaving behind less than 0.1% monomer distillation bottoms. A subsequent distillation was performed to separate the dimer from the trimer+ with less than 5% trimer remained in the dimer cut. The dimer cut was subsequently hydrogenated without isomerization.

Example 17

Hexadecene with 93% alpha olefin and less than 8% branched and internal olefins was oligomerized under $BF_3$ with a co-catalyst composition of Butanol and Butyl Acetate. The reaction was held at 80° C. during semi-continuous addition of olefins and co-catalyst. The residence time was 90 minutes. The unreacted monomer was then distilled off, leaving behind less than 0.1% monomer distillation bottoms. A subsequent distillation was performed to separate the dimer from the trimer+ with less than 5% trimer remained in the dimer cut. The dimer cut was subsequently hydrogenated without isomerization.

Example 18

Hexadecene with 75% alpha olefin and less than 1% branched and internal olefins was oligomerized under $BF_3$ with a co-catalyst composition of Butanol and Butyl Acetate. The reaction was held at 50° C. during semi-continuous addition of olefins and co-catalyst. The residence time was 120 minutes. The unreacted monomer was then distilled off, leaving behind less than 0.1% monomer distillation bottoms. A subsequent distillation was performed to separate the dimer from the trimer+ with less than 5% trimer remained in the dimer cut. The dimer cut was subsequently hydrogenated without isomerization.

Example 19

Hexadecene with 60% alpha olefin and less than 1% branched and internal olefins was oligomerized under $BF_3$ with a co-catalyst composition of Butanol and Butyl Acetate. The reaction was held at 50° C. during semi-continuous addition of olefins and co-catalyst. The residence time was 120 minutes. The unreacted monomer was then distilled off, leaving behind less than 0.1% monomer distillation bottoms. A subsequent distillation was performed to separate the dimer from the trimer+ with less than 5% trimer remained in the dimer cut. The dimer cut was subsequently hydrogenated without isomerization.

Example 20

Hexadecene with 60% alpha olefin and less than 1% branched and internal olefins was oligomerized under $BF_3$ with a co-catalyst composition of Butanol and Butyl Acetate. The reaction was held at 30° C. during semi-continuous addition of olefins and co-catalyst. The residence time was 120 minutes. The unreacted monomer was then distilled off, leaving behind less than 0.1% monomer distillation bottoms. A subsequent distillation was performed to separate the dimer from the trimer+ with less than 5% trimer remained in the dimer cut. The dimer cut was subsequently hydrogenated without isomerization.

Example 21

Hexadecene with 45% alpha olefin and less than 1% branched and internal olefins was oligomerized under $BF_3$ with a co-catalyst composition of Butanol and Butyl Acetate. The reaction was held at 50° C. during semi-continuous addition of olefins and co-catalyst. The residence time was 120 minutes. The unreacted monomer was then distilled off, leaving behind less than 0.1% monomer distillation bottoms. A subsequent distillation was performed to separate the dimer from the trimer+ with less than 5% trimer remained in the dimer cut. The dimer cut was subsequently hydrogenated without isomerization.

That which is claimed is:

1. A process for preparing a base stock, comprising:
    (i) providing an olefinic feedstock comprising C16 to C20 olefins which comprises less than 40 wt % branched olefins and greater than 40 wt % alpha olefins;
    (ii) oligomerizing the olefinic feedstock using a boron trifluoride catalyst at a reaction temperature in a range of from 20-60° C., while controlling the reaction conditions to obtain an intermediate having a dimers fraction such that the dimers fraction of the intermediate when saturated without hydroisomerization results in a saturated dimer with a branching proximity of 27-35; and
    (iii) hydroisomerizing at least a portion of the intermediate obtained from step (ii) using a metal impregnated one-dimensional, 10-member ring zeolite catalyst to achieve a C28+ product with BP/BI≥−0.6037* (Internal alkyl branching per molecule)+2.0 and on average 0.3 to 1.5 methyl branches on the fifth or greater position per molecule.

2. The process of claim 1, wherein the olefinic feedstock comprises greater than 50 wt % alpha olefins.

3. The process of claim 2, wherein the olefinic feedstock comprises less than 8 wt % branched olefins.

4. The process of claim 1, wherein the olefinic feedstock comprises greater than 70 wt % alpha olefins.

5. The process of claim 1, wherein the boron trifluoride catalyst used in the oligomerizing of (ii) further comprises an alcohol promoter, and an ester promoter.

6. The process of claim 1, wherein the residence time for the oligomerization reaction ranges from 60-180 minutes.

7. The process of claim 2, further comprising recovering the intermediate, removing unreacted monomer from the intermediate, and recovering a resulting intermediate prior to step (iii).

8. The process of claim 7, wherein the unreacted monomer removed is recycled to the olefinic feedstock of step (i).

9. The process of claim 7, further comprising hydrogenating the resulting intermediate to create a hydrogenated intermediate, the hydrogenated intermediate is then subjected to the hydroisomerization of step (iii); and
    recovering a product from the hydroisomerization and separating product from the hydroisomerization into a fraction comprising greater than 95 wt % dimers having a maximum carbon number of 40, and a fraction comprising greater than 95 wt % trimers and higher oligomers having a minimum carbon number of 42.

10. The process of claim 7, wherein the resulting intermediate is separated into a fraction comprising greater than 95 wt % dimers having a maximum carbon number of 40, and a fraction comprising greater than 95% trimers and higher oligomers having a minimum carbon number of 42.

11. The process of claim 10, further comprising hydroisomerizing each of the fractions separately.

12. The process of claim 7, wherein the resulting intermediate is further hydrogenated to create a hydrogenated intermediate, with the hydrogenated intermediate comprising dimers having a maximum carbon number of 40 and a branching proximity from 28-32.

13. The process of claim 2, wherein the hydroisomerizing is conducted under a pressure of 100-800 psig; a temperature in a range of from 290-350° C., and a hydrogen flow rate of 500-3500 scf/bbl.

14. A process for preparing a base stock, comprising:
    (i) providing an olefinic feedstock comprising less than 8 wt % branched monomeric olefins and greater than 50 wt % monomeric alpha olefins, with the monomeric olefins having a carbon number in the range of from C16-C20;
    (ii) conducting an oligomerization reaction with the olefinic feedstock of (i) at a temperature in the range of from 20 to 60° C., over a BuOH and BuAc co-catalyst, with a reaction residence time of from 60-180 minutes, in a semi-batch or continuous stirred tank reactor, while controlling the reaction conditions to obtain an intermediate with a dimers fraction such that the dimers fraction of the intermediate when saturated without hydroisomerization results in a saturated dimer with a branching proximity of 27-35;
    (iii) recovering the intermediate from the oligomerization reaction in step (ii), removing unreacted monomer by distillation, and recovering a resulting intermediate from the distillation;
    (iv) hydrogenating the resulting intermediate recovered from the distillation in (iii);
    (v) recovering a hydrogenation product from the hydrogenation in (iv) and hydroisomerizing the hydrogenation product over a metal impregnated, one-dimensional zeolite with a 10-member ring at a pressure in the range of from 100-800 psig; a temperature in the range of from 290-350° C.; and at a hydrogen flow rate of 500-3500 scf/bbl to produce a hydroisomerized product;
    (vi) recycling the unreacted monomer removed in (iii) to the olefinic feedstock in (i); and
    (vii) separating a dimers fraction and a trimers and higher oligomers fraction from the hydroisomerized product of step (v), with the dimers fraction comprising greater than or equal to 95 wt % dimers having a maximum carbon number of 40.

15. A process for preparing a base stock, comprising:
    providing an olefinic feedstock comprising less than 8 wt % branched monomeric olefins and greater than 50 wt % monomeric alpha olefins, with the monomeric olefins having a carbon number in the range of from C16-C20;
    (ii) conducting an oligomerization reaction with the olefinic feedstock of (i) at a temperature in the range of from 20 to 60° C., over a BuOH and BuAc co-catalyst, with a reaction residence time of from 60-180 minutes, in a semi-batch or continuous stirred tank reactor, while controlling the reaction conditions to obtain an intermediate with a dimers fraction such that the dimers fraction of the intermediate when saturated without hydroisomerization results in a saturated dimer with a branching proximity of 27-35;

(iii) recovering the intermediate from the oligomerization reaction in step (ii), removing unreacted monomer by distillation;

(iv) recovering a bottoms product from the distillation in (iii) and hydroisomerizing the bottoms product over a metal impregnated, one-dimensional zeolite with a 10-member ring at a pressure in the range of from 100-800 psig; a temperature in the range of from 290-350° C.;

and at a hydrogen flow rate of 500-3500 scf/bbl;

(v) recycling the unreacted monomer removed in (iii) to the olefinic feedstock in (i); and (vi) recovering a hydroisomerization product from the hydroisomerization in (iv) and separating the hydroisomerization product into a dimer fraction comprising dimers having a carbon number in the range of from C28-C40, and a trimer and higher oligomers fraction comprising compounds having a carbon number of 42 and higher.

16. A process for preparing a base stock, comprising:

providing an olefinic feedstock comprising less than 8 wt % branched monomeric olefins and greater than 50 wt % monomeric alpha olefins, with the monomeric olefins having a carbon number in the range of from C16-C20;

(ii) conducting an oligomerization reaction with the olefinic feedstock of (i) at a temperature in the range of from 20 to 60° C., over a BuOH and BuAc co-catalyst, with a reaction residence time of from 60-180 minutes, in a semi-batch or continuous stirred tank reactor, while controlling the reaction conditions to obtain an intermediate with a dimers/fraction such that the dimers fraction of the intermediate when saturated without hydroisomerization results in a saturated dimer with a branching proximity of 27-35;

(iii) recovering the intermediate from the oligomerization reaction in step (ii), removing unreacted monomer by distillation, and recovering a bottoms distillation product;

(iv) separating a dimers fraction and a trimers and higher oligomers fraction from the bottoms distillation product of (iii), with the dimers fraction comprising greater than or equal to 95% compounds having a maximum carbon number of 40, and with the trimers and higher oligomers fraction comprising compounds having a carbon number of 42 and greater; and (v) hydroisomerizing each fraction in (iv) separately over a metal impregnated, one-dimensional zeolite with a 10-member ring at a pressure in the range of from 100-800 psig; a temperature in the range of from 290-350° C.; and at a hydrogen flow rate of 500-3500 scf/bbl.

17. The process of claim 1, wherein the metal impregnated 10 member ring zeolite catalyst is impregnated with Pt, Pd, or a mixture thereof.

* * * * *